(12) United States Patent
Rogers

(10) Patent No.: US 7,001,359 B2
(45) Date of Patent: Feb. 21, 2006

(54) IMPLANTABLE THERAPEUTIC SUBSTANCE INFUSION DEVICE WITH ACTIVE LONGEVITY PROJECTION

(75) Inventor: Charles R. Rogers, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 54 days.

(21) Appl. No.: 09/809,809

(22) Filed: Mar. 16, 2001

(65) Prior Publication Data

US 2002/0161328 A1 Oct. 31, 2002

(51) Int. Cl.
A61M 1/00 (2006.01)

(52) U.S. Cl. .................. 604/118; 604/131; 604/65

(58) Field of Classification Search .................. 604/65, 604/66, 67, 118–123, 131–155, 890.1, 891.1, 604/30, 500, 502, 503, 288.01
See application file for complete search history.

(56) References Cited

U.S. PATENT DOCUMENTS

| | | |
|---|---|---|
| 4,026,305 A | 5/1977 | Brownlee et al. |
| 4,041,955 A | 8/1977 | Kelly et al. |
| 4,071,032 A | 1/1978 | Schulman |
| 4,082,097 A | 4/1978 | Mann et al. |
| 4,142,533 A | 3/1979 | Brownlee et al. |
| 4,248,237 A | 2/1981 | Kenny |
| 4,254,775 A | 3/1981 | Langer |
| 4,313,079 A | 1/1982 | Lee |
| 4,373,527 A | 2/1983 | Fischell |
| 4,390,020 A | 6/1983 | Herpers |
| 4,448,197 A | 5/1984 | Nappholz et al. |
| 4,542,532 A | 9/1985 | McQuilkin |
| 4,550,370 A | 10/1985 | Baker |
| 4,556,061 A | 12/1985 | Barreras et al. |
| RE32,361 E | 2/1987 | Duggan |
| 4,677,363 A | 6/1987 | Kopmann |

(Continued)

FOREIGN PATENT DOCUMENTS

IT 1153910 B 1/1987

(Continued)

OTHER PUBLICATIONS

"Meta DDDR Model 1254 Physician's Manual", Medtronic, Inc.

(Continued)

Primary Examiner—Long V. Le
Assistant Examiner—Ann Y Lam
(74) Attorney, Agent, or Firm—John W. Albrecht; Eric R. Waldkoetter

(57) ABSTRACT

A medical device known as an implantable therapeutic substance delivery device is configured for implanting in humans to deliver a therapeutic substance such as pharmaceutical compositions, genetic materials, and biologics to treat a variety of medical conditions such as pain, spasticity, cancer, and many other conditions. The infusion device embodiment has active longevity projection that more accurately predicts an elective replacement period for the infusion device to increase the infusion device's effective life, reduce the need for a clinician to perform static longevity forecasts for therapy changes, facilitate elective replacement scheduling for the convenience of the patient and clinician, and many other improvements. The infusion device has a housing, a power source, a therapeutic substance reservoir, a therapeutic substance pump, and electronics. Many embodiments of the therapeutic substance delivery device with active longevity projection and its methods of operation are possible.

2 Claims, 12 Drawing Sheets

Examples of 'Elective Replacement' and 'End of Life' -vs- Flow Rate:

| Flow (ul/day) | Battery Longevity (yrs) | Accumulated Pump Revs | ERI Criteria | EOL Criteria | Longevity Determined By: |
|---|---|---|---|---|---|
| 50.00 | 23.96 | 7283.18 | 9yrs (less 90 days) | 9 Years | Corrosion |
| 100.00 | 20.91 | 12688.87 | 9yrs (less 90 days) | 9 Years | Corrosion |
| 250.00 | 15.11 | 22879.50 | 9yrs (less 90 days) | 9 Years | Corrosion |
| 500.00 | 10.30 | 31247.45 | 9yrs (less 90 days) | 9 Years | Corrosion |
| 750.00 | 7.80 | 35587.35 | 2.57 Volts | 2.5 volts | Battery |
| 1000.00 | 6.27 | 38243.64 | 2.59 Volts | 2.5 volts | Battery |
| 1250.00 | 5.24 | 40036.90 | 2.61 Volts | 2.5 volts | Battery |
| 1500.00 | 4.50 | 41328.98 | 38750 Revs | 41000 Revs | Mechanical Wear |
| 2000.00 | 3.50 | 43066.44 | 38000 Revs | 41000 Revs | Mechanical Wear |

U.S. PATENT DOCUMENTS

| | | |
|---|---|---|
| 5,006,997 A | 4/1991 | Reich |
| 5,049,141 A * | 9/1991 | Olive ................... 604/891.1 |
| 5,080,096 A | 1/1992 | Hooper et al. |
| 5,107,833 A | 4/1992 | Barsness |
| 5,117,825 A | 6/1992 | Grevious |
| 5,127,404 A | 7/1992 | Wyborny et al. |
| 5,168,871 A | 12/1992 | Grevious |
| 5,292,343 A | 3/1994 | Blanchette et al. |
| 5,314,450 A | 5/1994 | Thompson |
| 5,324,315 A | 6/1994 | Grevious |
| 5,344,431 A | 9/1994 | Merritt et al. |
| 5,350,411 A | 9/1994 | Ryan et al. |
| 5,354,319 A | 10/1994 | Wyborny et al. |
| 5,369,364 A | 11/1994 | Renirie et al. |
| 5,370,668 A | 12/1994 | Shelton et al. |
| 5,383,909 A | 1/1995 | Keimel |
| 5,391,193 A | 2/1995 | Thompson |
| 5,402,070 A | 3/1995 | Shelton et al. |
| 5,402,794 A | 4/1995 | Wahlstrand et al. |
| 5,411,537 A | 5/1995 | Munshi et al. |
| 5,458,624 A | 10/1995 | Renirie et al. |
| 5,517,008 A * | 5/1996 | Francart, Jr. ............... 235/91 F |
| 5,576,503 A * | 11/1996 | Nabity et al. ............ 73/863.01 |
| 5,591,217 A | 1/1997 | Barreras |
| 5,620,474 A | 4/1997 | Koopman |
| 5,693,076 A | 12/1997 | Kaemmerer |
| 5,741,307 A | 4/1998 | Kroll |
| 5,741,313 A | 4/1998 | Davis et al. |
| 5,744,931 A | 4/1998 | Arai et al. |
| 5,752,976 A | 5/1998 | Duffin et al. |
| 5,766,232 A | 6/1998 | Grevious et al. |
| 5,769,873 A | 6/1998 | Zadeh |
| 5,769,877 A | 6/1998 | Barreras, Sr. |
| 5,807,397 A | 9/1998 | Barreras |
| 5,861,019 A | 1/1999 | Sun et al. |
| 5,904,708 A | 5/1999 | Goedeke |
| 5,994,876 A | 11/1999 | Canny et al. |
| 6,016,448 A | 1/2000 | Busacker et al. |
| 6,099,495 A | 8/2000 | Kinghorn et al. |
| 6,108,579 A * | 8/2000 | Snell et al. ................... 607/29 |
| 6,112,116 A | 8/2000 | Fischell et al. |
| 6,148,235 A | 11/2000 | Kuiper |
| 6,154,675 A | 11/2000 | Juran et al. |
| 6,166,518 A | 12/2000 | Echarri et al. |
| 6,167,309 A | 12/2000 | Lyden |
| 6,185,461 B1 | 2/2001 | Er |
| 6,198,968 B1 | 3/2001 | Prutchi et al. |
| 6,272,379 B1 | 8/2001 | Fischell et al. |
| 6,400,988 B1 | 6/2002 | Gurewitsch |
| 6,439,856 B1 * | 8/2002 | Ivey ........................... 417/63 |
| 6,490,484 B1 | 12/2002 | Dooley et al. |
| 6,584,355 B1 | 6/2003 | Stessman |
| 2002/0161328 A1 | 10/2002 | Rogers |
| 2003/0065366 A1 | 4/2003 | Merritt et al. |

FOREIGN PATENT DOCUMENTS

| | | |
|---|---|---|
| WO | WO 91/10471 A1 | 7/1991 |
| WO | WO 96/20754 A1 | 7/1996 |
| WO | WO 99/14612 A | 3/1999 |
| WO | WO 00/24459 A1 | 5/2000 |
| WO | WO 01/08749 A1 | 2/2001 |
| WO | WO 02/49718 A1 | 6/2002 |
| WO | WO 02/074368 A1 | 9/2002 |

OTHER PUBLICATIONS

"Displaying a Summary of Pacemaker Status", pp. 4-6—4-10.

* cited by examiner

Examples of 'Elective Replacement' and 'End of Life' -vs- Flow Rate:

| Flow (ul/day) | Battery Longevity (yrs) | Accumulated Pump Revs | ERI Criteria | EOL Criteria | Longevity Determined By: |
|---|---|---|---|---|---|
| 50.00 | 23.96 | 7283.18 | 9yrs (less 90 days) | 9 Years | Corrosion |
| 100.00 | 20.91 | 12688.87 | 9yrs (less 90 days) | 9 Years | Corrosion |
| 250.00 | 15.11 | 22879.50 | 9yrs (less 90 days) | 9 Years | Corrosion |
| 500.00 | 10.30 | 31247.45 | 9yrs (less 90 days) | 9 Years | Corrosion |
| 750.00 | 7.80 | 35587.35 | 2.57 Volts | 2.5 volts | Battery |
| 1000.00 | 6.27 | 38243.64 | 2.59 Volts | 2.5 volts | Battery |
| 1250.00 | 5.24 | 40036.90 | 2.61 Volts | 2.5 volts | Battery |
| 1500.00 | 4.50 | 41328.98 | 38750 Revs | 41000 Revs | Mechanical Wear |
| 2000.00 | 3.50 | 43066.44 | 38000 Revs | 41000 Revs | Mechanical Wear |

FIG. 7

IMPLANTABLE THERAPEUTIC SUBSTANCE INFUSION DEVICE WITH ACTIVE LONGEVITY PROJECTION

BACKGROUND OF THE INVENTION

This disclosure relates to a medical device and more particularly to an implantable therapeutic substance infusion device also known as an implantable drug pump.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable therapeutic substance infusion device.

An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured, so the device can be replenished with therapeutic substance through a septum while the device is implanted, so the time the device can be implanted may not be limited by therapeutic substance capacity. An example of an implantable therapeutic substance infusion is shown in Medtronic, Inc. product brochure entitled "SynchroMed® Infusion System" (1995).

Electrically powered implanted therapeutic substance infusion devices can require replacement once implanted due factors such as battery consumption, corrosive damage, and mechanical wear. Since replacement of the implanted device requires an invasive procedure of explanting the existing device and implanting a new device, it is desirable to only replace the infusion device when replacement is required. Replacement of previous implantable infusion devices was typically scheduled based upon a worst-case statically forecasted elective replacement period. The worst-case scenario typically resulting in the implanted infusion device being replaced several months or even years before the implanted infusion device required replacement. Some previous implantable pulse generators such as pacemakers have monitored a single sensed battery condition to estimate replacement time for the implanted device or battery such as shown in U.S. Pat. No. 6,167,309 "Method For Monitoring End Of Life For Battery" by Lyden (Dec. 26, 2000).

For the foregoing reasons, there is a need for an implantable therapeutic substance infusion device with active longevity prediction to increase the infusion device's effective life, reduce the need for a clinician to perform static longevity forecasts for therapy changes, facilitate elective replacement scheduling for the convenience of the patient and clinician, and many other improvements.

SUMMARY OF THE INVENTION

An implantable therapeutic substance infusion device embodiment with active longevity projection more accurately predicts an elective replacement period for the infusion device to increase the infusion device's effective life, reduce the need for a clinician to perform static longevity forecasts for therapy changes, facilitate elective replacement scheduling for the convenience of the patient and clinician, and many other improvements. Active longevity projection is accomplished with a longevity prediction program that correlates at least one preset parameter to at least one sensed parameter to calculate an elective replacement period for the infusion device. The preset parameter is resides in memory and is indicative of longevity of the infusion device. The sensed parameter is accessible by the processor indicative of longevity of the infusion device. The infusion device has a housing; a power source; a therapeutic substance reservoir configured for containing a therapeutic substance and being refilled with the therapeutic substance while implanted; a therapeutic substance pump fluidly coupled to the therapeutic substance reservoir, and electrically coupled to the power source; and, electronics electrically coupled to the power source and coupled to the therapeutic substance pump. The electronics include a processor; memory coupled to the processor; an infusion program residing in memory, the infusion program capable of being modified once the therapeutic substance infusion device is implanted; and, transceiver circuitry coupled to the processor for externally receiving and transmitting therapeutic substance infusion device information. Many embodiments of the therapeutic substance delivery device with active longevity projection and its methods of operation are possible.

BRIEF DESCRIPTION OF THE DRAWINGS

FIG. 7 shows a table for longevity determination based up scenarios for an implantable therapeutic substance infusion device embodiment;

DETAILED DESCRIPTION OF THE PREFERRED EMBODIMENTS

Figure 1:
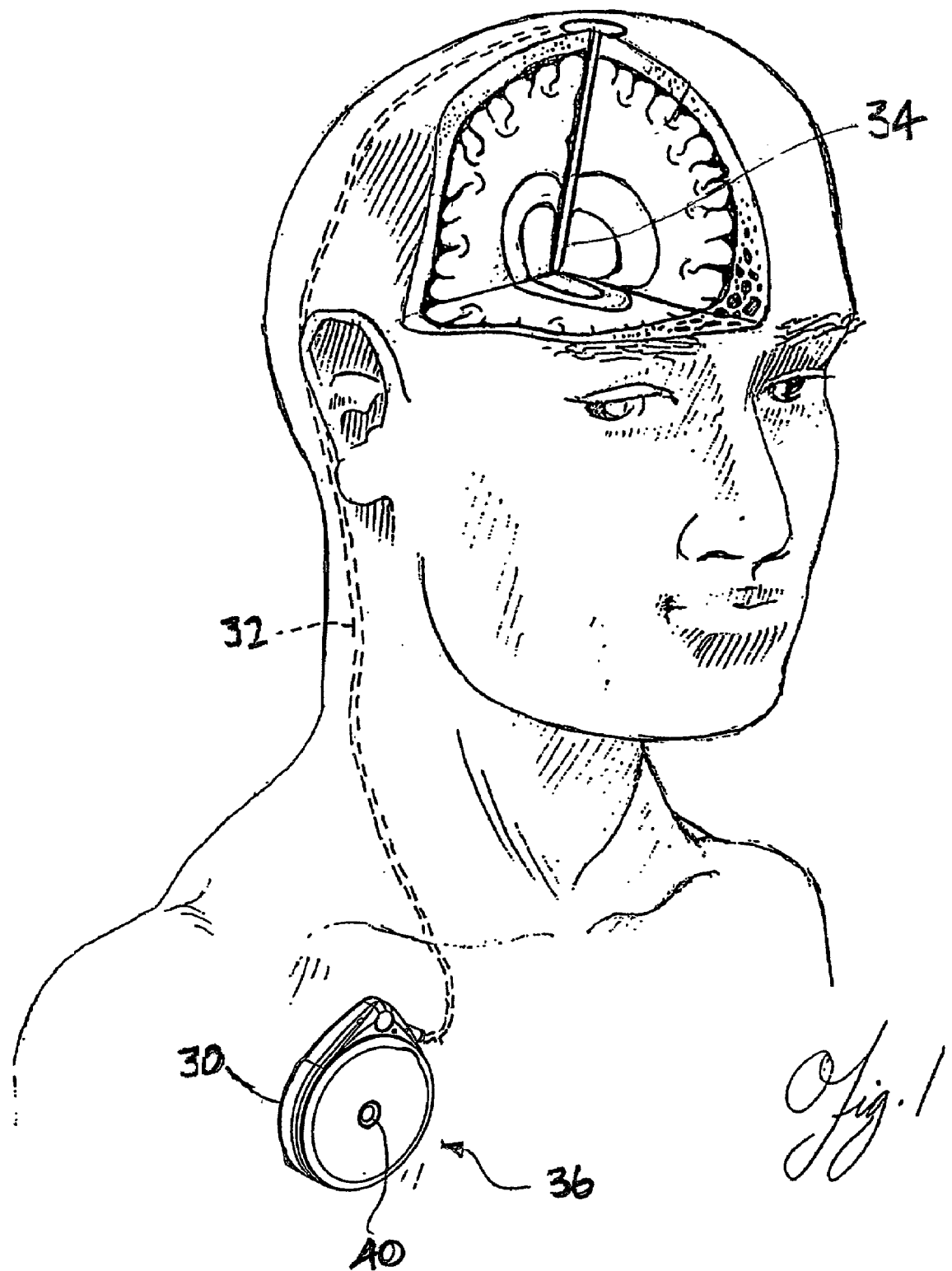
FIG. 1 shows the environment of an implantable therapeutic substance infusion device embodiment.
Figure 2:
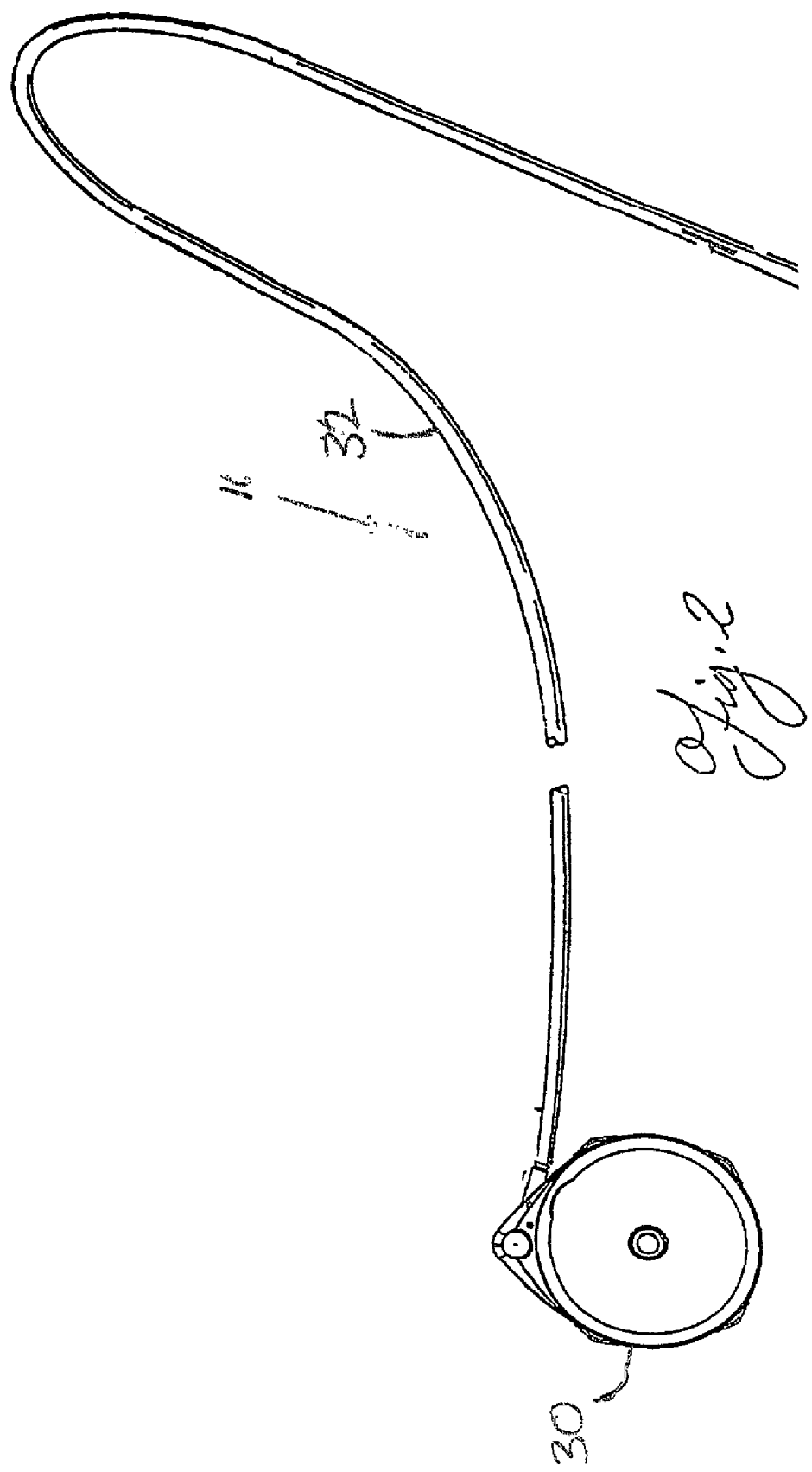
FIG. 2 shows an implantable therapeutic substance infusion device with catheter embodiment.
Figure 3:
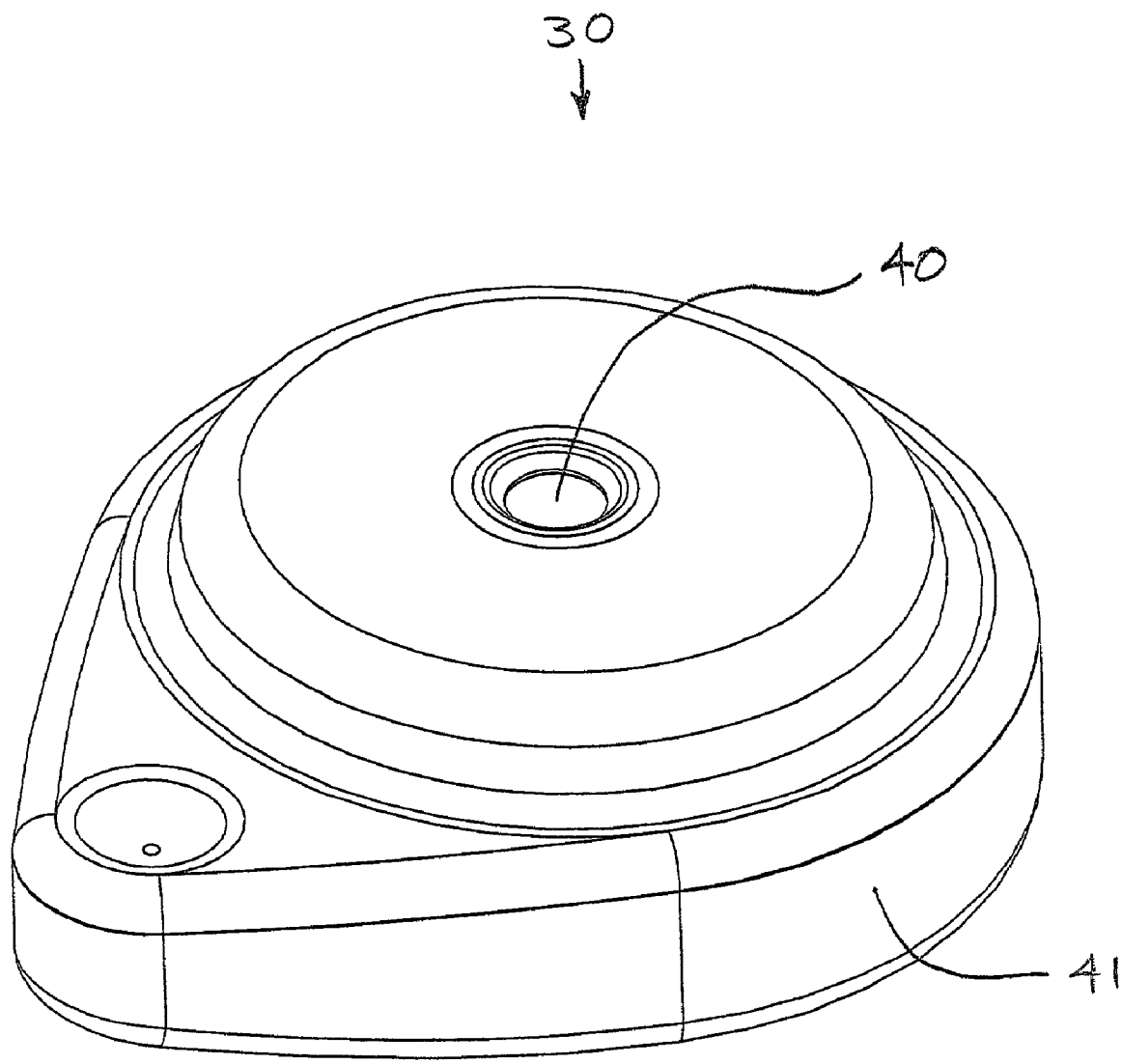
FIG. 3 shows an implantable therapeutic substance infusion device embodiment.
Figure 4:
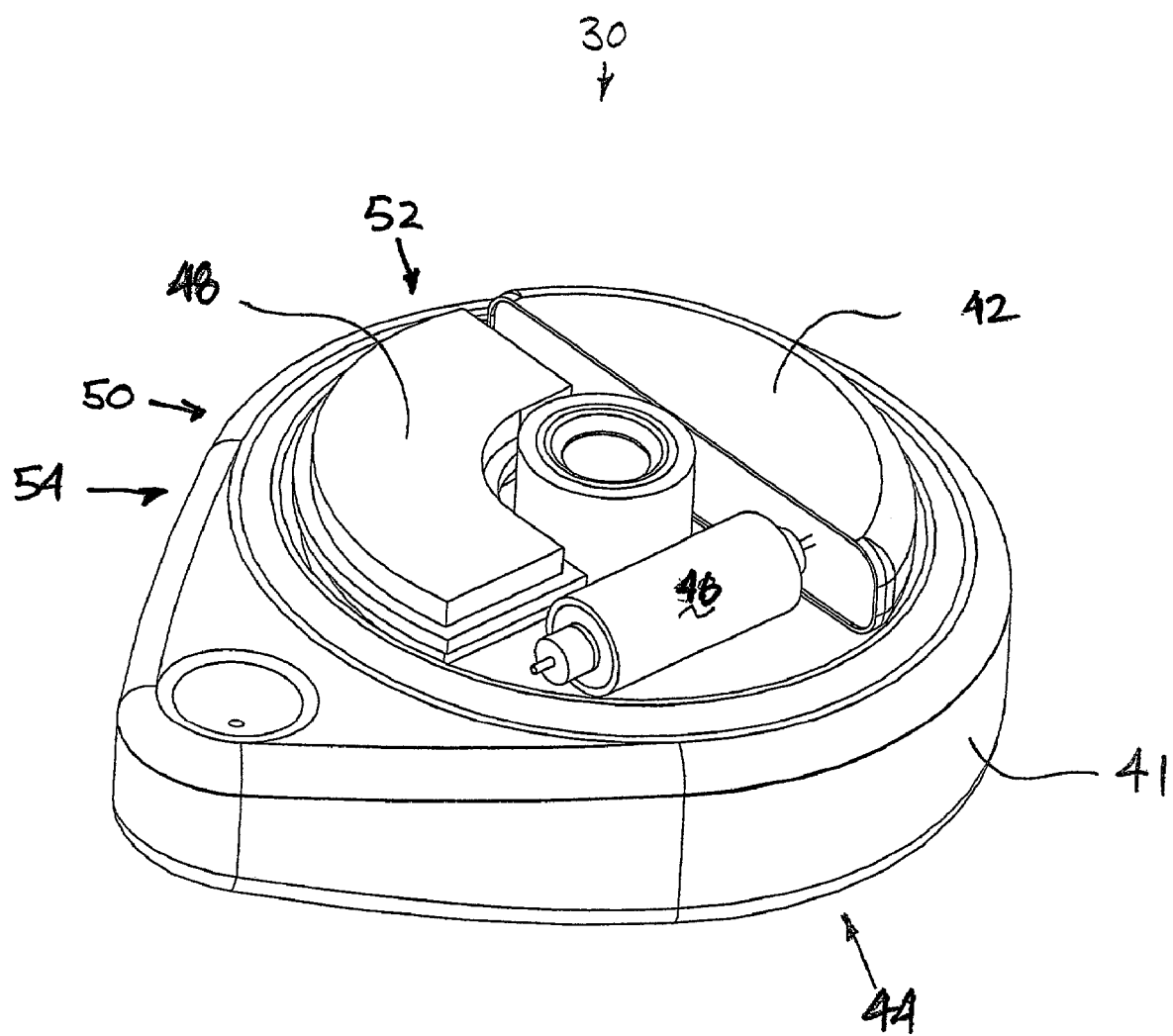
FIG. 4 shows the implantable therapeutic substance infusion device of FIG. 3 with a portion of a housing removed to show a piston pump embodiment.
Figure 5:
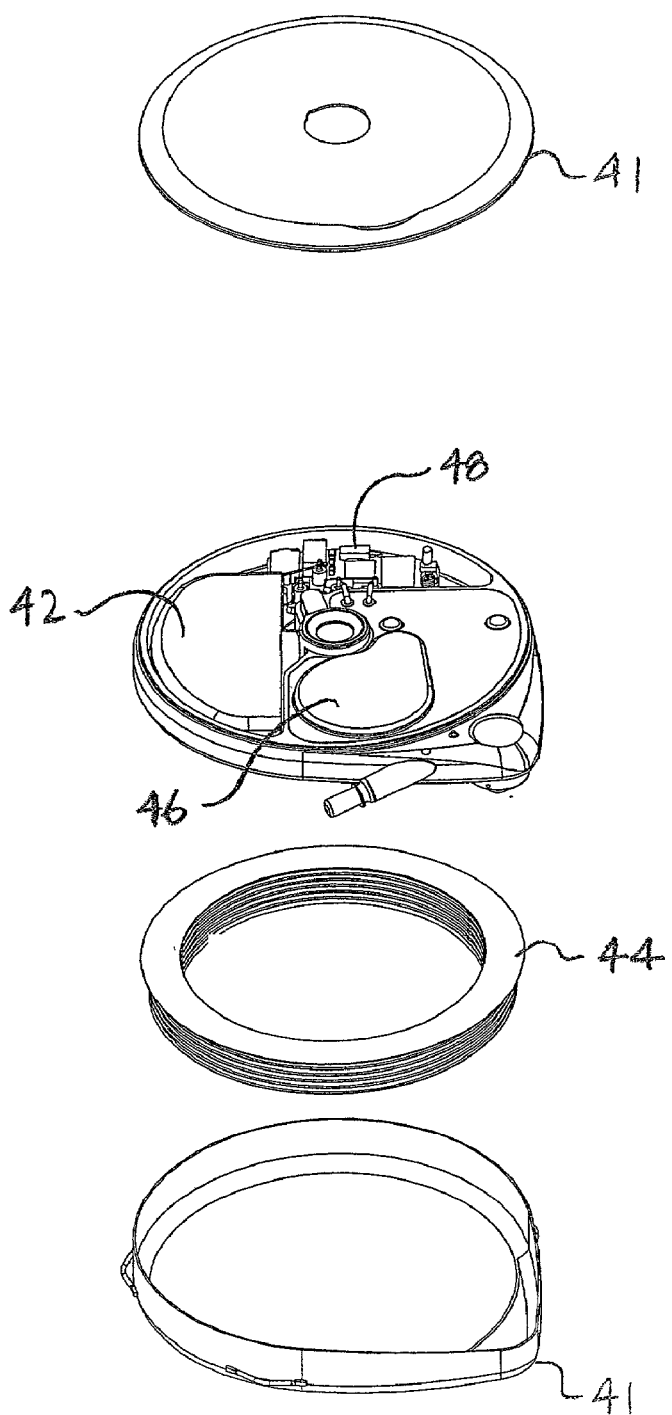
FIG. 5 shows an exploded view of an implantable therapeutic substance infusion device with peristaltic pump embodiment.

FIG. 1 shows the environment of an implantable medical device known as an implantable therapeutic substance delivery device 30, also known as a drug pump, having a permanent magnet solenoid pump embodiment. The therapeutic substance delivery device 30 can be used for a wide variety of therapies such as pain, spasticity, cancer, and many other medical conditions. The implantable therapeutic substance delivery device 30 is typically implanted by a clinician such as a surgeon in a sterile surgical procedure performed under local, regional, or general anesthesia. Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The implantable therapeutic substance delivery device 30 is generally implanted subcutaneously about 2.5 cm (1.0 inch) beneath the skin where there is sufficient subcutaneous tissue to support the implanted system. Once the therapeutic substance delivery device 30 is subcutaneously implanted into the patient, the incision can be sutured closed and the therapeutic substance delivery device 30 can begin operation.

The therapeutic substance delivery device 30 operates to infuse a therapeutic substance 36 at a programmed rate into a patient 38. The therapeutic substance 36 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 can be replenished in some embodiments of the implanted therapeutic substance delivery device 30 by inserting a non-coring needle connected to a syringe filled with therapeutic substance 36 through the patient's skin into a septum 40 on the therapeutic substance delivery device 30 to fill the implanted device. If the therapeutic substance delivery device 30 requires replacement due to conditions such as battery depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 6:
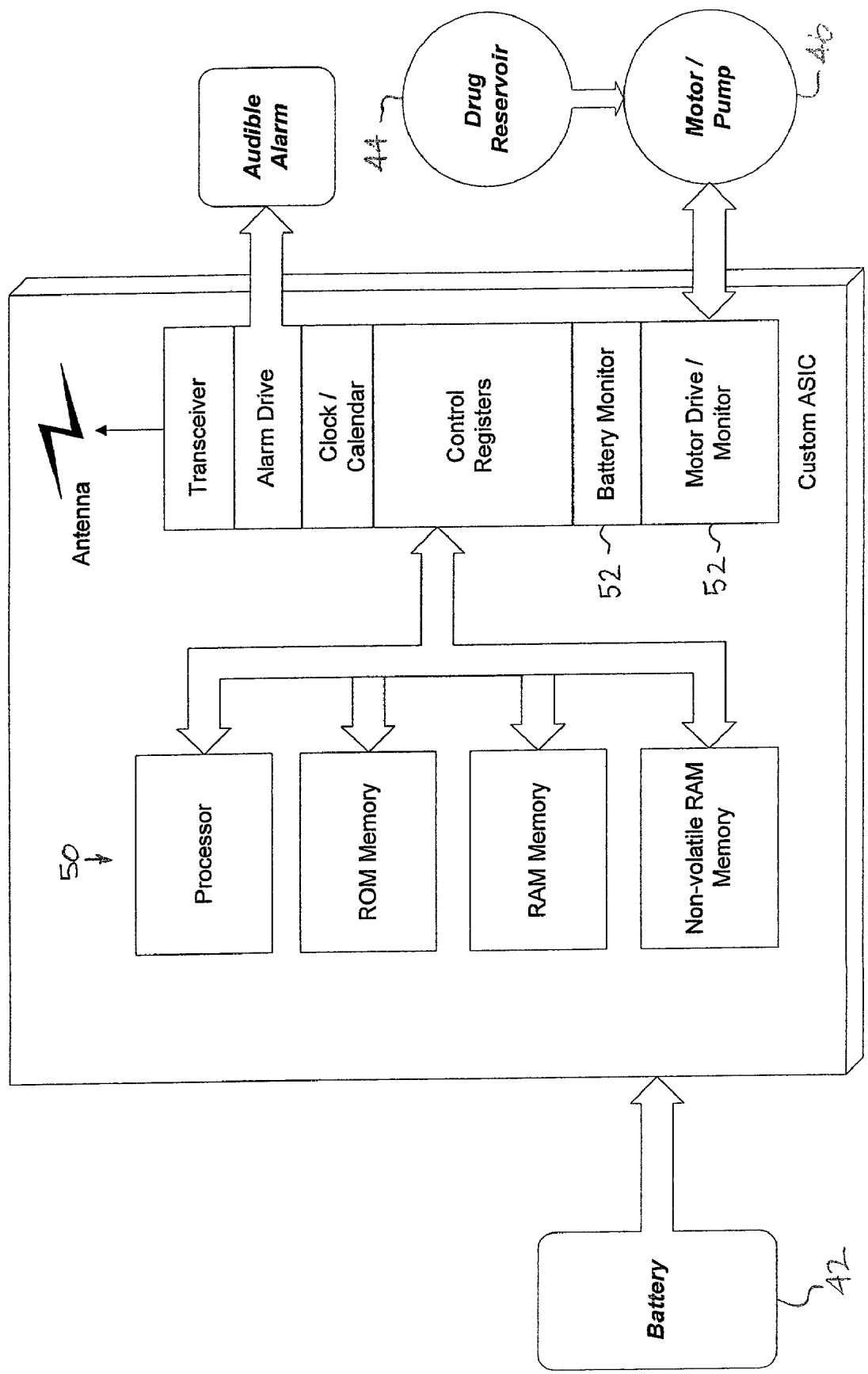
FIG. 6 shows a block diagram of an implantable therapeutic substance infusion device embodiment.

FIGS. 2–5 show views of an implantable therapeutic substance infusion device embodiment with active longevity projection, and FIG. 6 shows a block diagram device embodiment. The implantable therapeutic substance infusion device with active longevity projection comprises a housing 41, a power source 42, a therapeutic substance reservoir 44, a therapeutic substance pump 46, electronics 48, at least one preset longevity parameter 50, and at least one sensed longevity parameter 52. The housing 41 is manufactured from a material that is biocompatible and hermetically sealed such as titanium, tantalum, stainless steel, plastic, ceramic, and the like. The power source 42 is carried in the housing 41. The power source 42 is selected to operate the therapeutic substance pump 46 and electronics 48 such as a lithium ion (Li+) battery, capacitor, and the like.

The therapeutic substance reservoir 44 is carried in the housing 41. The therapeutic substance reservoir 44 is configured for containing a therapeutic substance 36. The therapeutic substance reservoir 44 is configured to be refilled with therapeutic substance 36 while implanted. The therapeutic substance pump 46 is carried in the housing 41. The therapeutic substance pump 46 is fluidly coupled to the therapeutic substance reservoir 44 and electrically coupled to the power source 42. The therapeutic substance pump 46 is a pump 46 that is sufficient for infusing therapeutic substance 36 such as a piston pump (FIG. 4), a peristaltic pump (FIG. 5) that can be found in the SynchroMed® Infusion System available from Medtronic, Inc., or a pump powered by a stepper motor, an AC motor, a DC motor, an electrostatic diaphragm, a piezoelectric diaphragm, a piezoelectric motor, a solenoid, a shape memory alloy, and the like.

The electronics 48 are carried in the housing 41 and coupled to the therapeutic substance pump 46 and the power source 42. The electronics 48 include a processor, memory, an infusion program, and transceiver circuitry. The processor can be an Application Specific Integrated Circuit (ASIC) state machine, a gate array, controller, and the like. The electronics 48 are configured to control the therapeutic substance pump 46 infusion rate and can be configured to operate many other features such as patient alarms and the like. The infusion program resides in memory and is capable of being modified once the therapeutic substance infusion device is implanted. The transceiver circuitry is coupled to the processor for externally receiving and transmitting therapeutic substance infusion device information.

The preset longevity parameter 50 is at least one preset longevity parameter 50 residing in memory. The preset longevity parameter 50 serves as a means for storing at least one preset parameter 50 indicative of longevity of the implantable therapeutic substance infusion device. The preset longevity parameter 50 can be any parameter that correlates with the longevity of the implantable therapeutic substance infusion device 30 such as battery installation date, elective replacement battery voltage threshold, pre-end-of-life battery voltage threshold, end-of-life battery voltage threshold, implant time early replacement, end-of-life implant time, pump revolutions elective replacement, pump revolutions end-of-life, minimum torque margin, drug specific corrosion factors, and the like.

The sensed longevity parameter 52 is at least one sensed longevity parameter 52 accessible by the processor. The sensed longevity parameter 52 serves as a means for sensing at least one sensed parameter 52 indicative of longevity for the implantable therapeutic substance infusion device 30. The sensed longevity parameter 52 can be stored in memory that is accessible by the processor to permit the processor to access many sensed longevity parameters 52 that can be sampled and stored in memory over a desired period. The sensed longevity parameter 52 is any measurable parameter that correlates to longevity of the therapeutic substance infusion device 30 such as implant time, elapsed implant time, battery voltage, mechanical indication, and the like. The mechanical indication can be any parameter that either directly or indirectly measures a mechanical operation in the therapeutic substance infusion device 30 such as therapeutic substance pump 46 cycles, therapeutic substance pump 46 torque, corrosion, and the like. When the desired mechanical indication is therapeutic substance pump 46 cycles, one embodiment uses a motor drive monitor coupled to the electronics 48 for counting the number of therapeutic substance pump 46 cycles.

The longevity prediction program 54 resides in memory and serves as a means for predicting longevity of the implantable therapeutic substance infusion device 30 by correlating the preset parameter 50 to the sensed parameter 52 to calculate an elective replacement period for the implantable therapeutic substance infusion device 30. The longevity prediction program 54 reports an elective replacement indicator in advance of an end-of-life period for the implantable therapeutic substance infusion device 30. The elective replacement indicator can be annunciated audibly, tactilely, audibly, electrically by transceiver circuitry, and the like. The elective replacement indicator permits the implantable therapeutic substance infusion device 30 to be operated closer to the end-of-life period for the implanted therapeutic substance infusion device 30 thereby extending an effective life of the implantable therapeutic substance infusion device 30.

Some embodiments can include a longevity extension program 56 contained in memory. The longevity extension program 56 selectively implements predetermined functional limitations to the implantable therapeutic substance infusion device 30. By implementing function limitations, critical functionality of the implantable therapeutic substance infusion device 30 can be extended beyond the calculated end-of-life period for the implantable therapeutic substance infusion device 30. The predetermined functional limitations can be any function limitation that is not critical to the therapy being delivered to the patient such as limit audible alarm duration, limit audible alarm drive level, limit pump flow rate, limit pump bolus rate, and the like.

The implantable therapeutic substance infusion device 30 with active longevity projection can be understood using by considering the following prophetic examples based upon empirical data from a infusion device similar to the SynchroMed® Infusion System available from Medtronic, Inc. and the formulas described. FIG. 7 shows a table with data to indicate that longevity of a therapeutic substance infusion device 30 embodiment can be determined by different factors depending on how the infusion device 30 is operated. The factors that determine infusion device 30 longevity can be corrosion, battery 42 capacity, mechanical wear such as determined from the accumulated infusion pump 46 revolutions, and the like. Infusion device 30 corrosion effects are based upon empirical data and can vary according to the therapeutic substance 36 being infused. Battery 42 longevity was calculated with the following simplified $$BatteryLongevity \text{ (days)} = \frac{\text{battery energy}}{\left(\frac{\text{motor energy}}{\text{day}}\right) + \left(\frac{\text{hybrid energy}}{\text{day}}\right)} \quad \text{(Equation 1)}$$

battery energy is about 21,600 Joules based upon a battery rated at 3V, 2 amp-hours; motor energy also includes peristaltic pump 46 energy which is typically about 8 mJ/µL with a pumping volume of about 60 µL per motor revolution; and, hybrid electronics 48 have a current drain of about 5 µA. Mechanical wear longevity is based upon empirical data.

Figure 8:
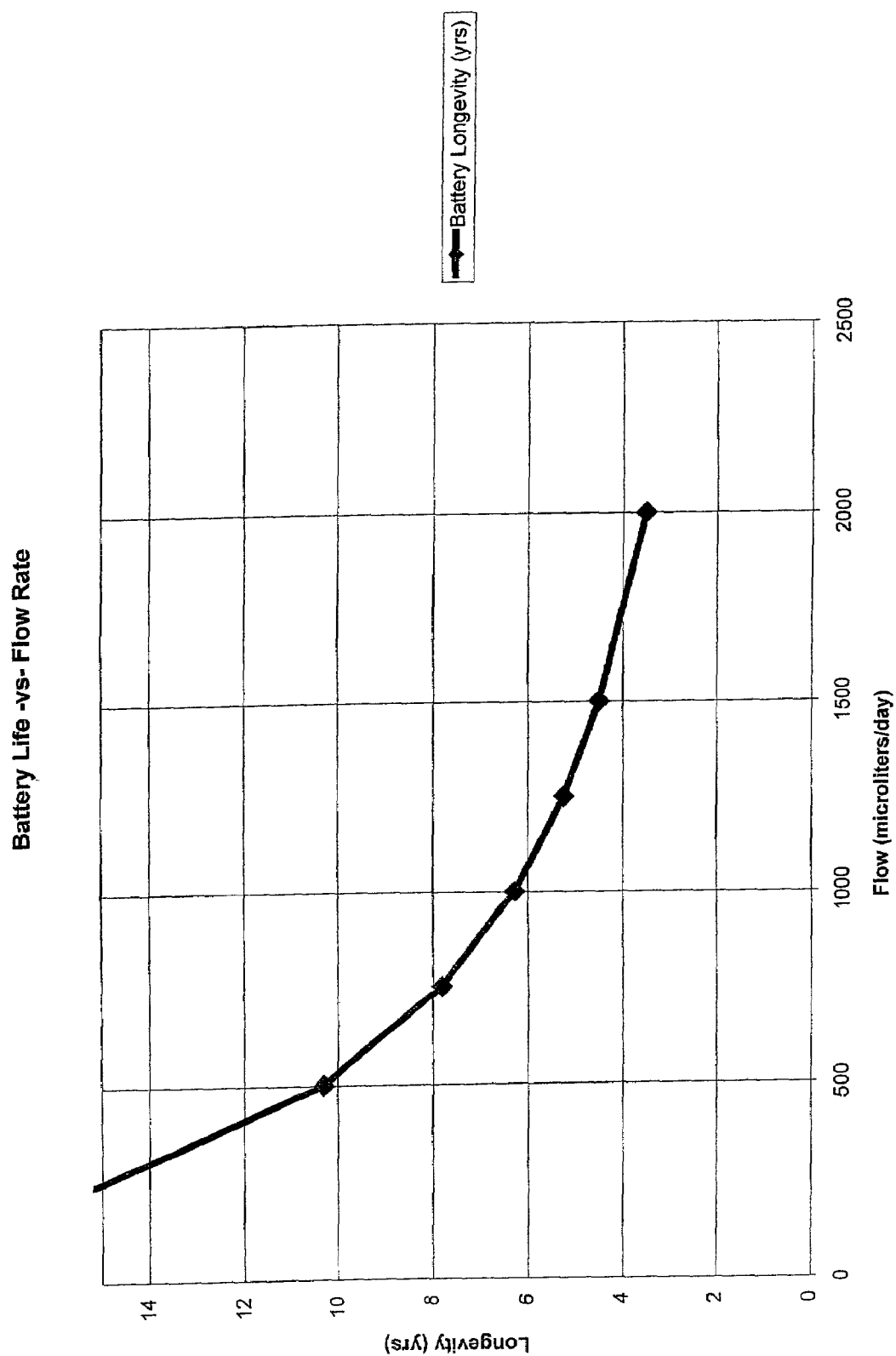
FIG. 8 shows a graph of battery life versus flow rate for an implantable therapeutic substance infusion device embodiment.
Figure 9:
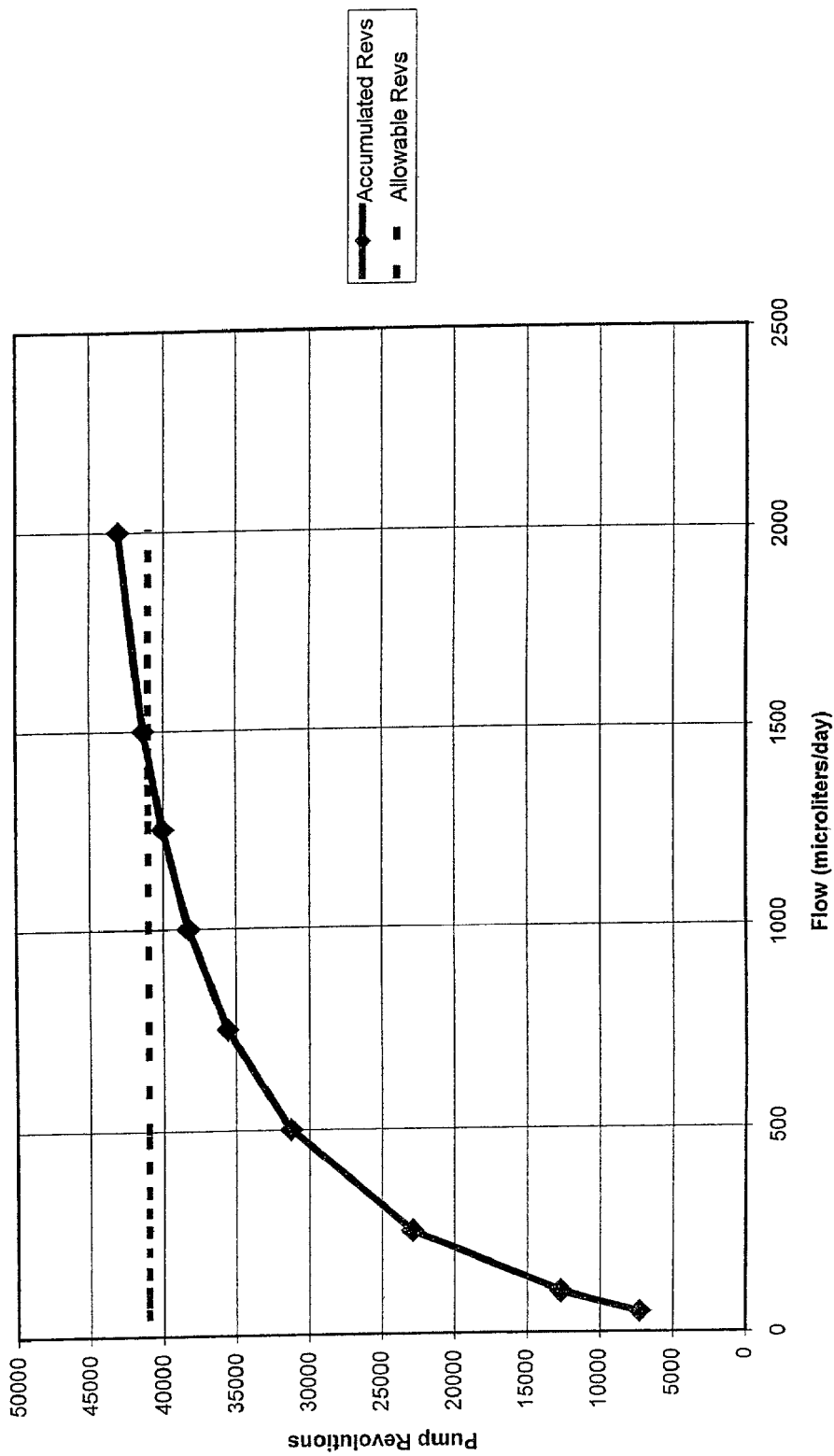
FIG. 9 shows a graph of pump revolutions versus flow rate for an implantable therapeutic substance infusion device embodiment.

FIG. 8 shows a graph of how battery 42 life can vary with flow rate, also known as infusion rate, of an implantable therapeutic substance infusion device 30 embodiment. The graph shows that as the daily delivery rate of the infusion pump 46 increases the battery 42 life decreases. FIG. 9 shows a graph of accumulated pump 46 revolutions versus flow rate to show how battery 42 life can very with accumulated pump 46 revolutions. The following formula can be used to calculate accumulated pump 46 revolutions.

$$\text{Accumulated Pump Revs} = (\mu L/\text{day}) / (\mu L/\text{rev}) \times \text{days} \quad \text{(Equation 2)}$$

where µL/day is the amount of therapeutic substance 36 to be infused during a 24 hour period and µL/rev is the number of peristaltic pump 46 revolutions to pump a µL of therapeutic substance 36. The graph in FIG. 9 shows that at flow rates of greater than about 1,500 µL per day the number of peristaltic pump 46 revolutions determines the life of the infusion device 30.

OPERATION

Figure 10:
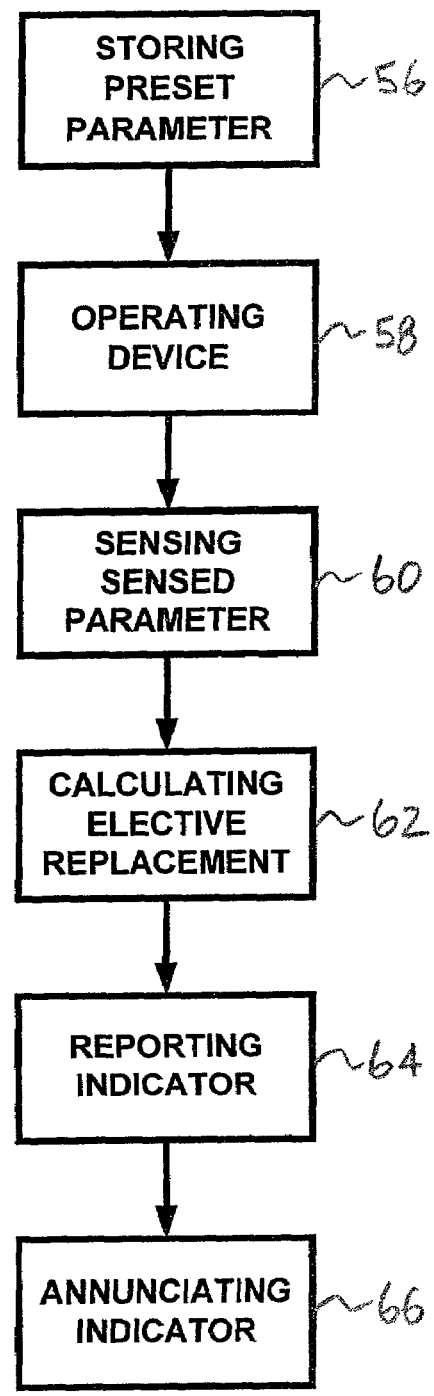
FIG. 10 shows a block diagram of a method for operating an implantable therapeutic substance infusion device embodiment with active longevity projection.

FIG. 10 shows a flow chart of a method for operating a therapeutic substance infusion device 30 with active longevity prediction embodiment. The method embodiment includes the elements of storing 56 at least one preset parameter 50, operating 58 the therapeutic substance infusion device 30, sensing 60 at least one sensed parameter 52, and calculating 62 an elective replacement period. Some embodiments can also include the elements of reporting 64 an elective replacement indicator and annunciating 66 the elective replacement indicator. The method embodiment can also be expressed as a computer software product that includes a medium readable by a processor. The medium has stored on it instructions for projecting the longevity of an implantable therapeutic substance infusion device 30. When expressed as a computer software product, each method embodiment element corresponds to a sequence of instructions executable by the processor. Embodiments of both the method of operating a therapeutic substance infusion device 30 with active longevity prediction and method expressed as a computer software product have many embodiments. Some embodiments can include elements corresponding to the previously therapeutic substance infusion device embodiments such as a motor drive monitor, a longevity extension program, and the like.

The method begins by storing 56 at least one preset parameter 50 accessible by the processor indicative of longevity for the implantable therapeutic substance infusion device 30. The preset parameter 50 can be stored in the therapeutic substance infusion device 30 in a variety of ways such as by the manufacturer before implantation, by the clinician before implantation, by the clinician after implantation, and the like. After storing 56 the preset parameter 50, the therapeutic substance infusion device 30 is implanted into the patient if it has not already been implanted.

The implantable therapeutic substance infusion device 30 begins operating 58 to infuse therapeutic substance 36 into a patient. Operation 58 of the implantable therapeutic substance infusion device 30 is typically controlled by a therapy program approved by the treating clinician. A wide variety of therapy programs can be used in the therapeutic substance infusion device with each therapy program having operating parameters that can affect the elective replacement period and end-of-life for the therapeutic substance infusion device such as drug formulation, therapy, implant time, and the like.

While the implantable therapeutic substance infusion device is operating 58, the device 30 senses at least one sensed parameter 52 that is indicative of longevity for the implantable therapeutic substance infusion device 30. The sensed parameter 52 any measurable parameter indicative of longevity such as elapsed implant time, battery voltage, a mechanical parameter, and the like. The mechanical parameter can be therapeutic substance pump 46 cycles, therapeutic substance pump 46 torque, corrosion, and the like.

The longevity prediction program calculates 62 an elective replacement period for the implantable therapeutic substance infusion device 30 by correlating the preset parameter 50 with the sensed parameter 52. In one embodiment, the longevity program implements logic such as can be derived from the table in FIG. 7 to calculate the elective replacement period that can be determined by corrosion, battery longevity, and mechanical longevity depending upon the manner the infusion pump operated.

The elective replacement period is reported 64 as an elective replacement indicator to permit the clinician or patient to consider options before replacement of the therapeutic substance infusion device 30 is required when the device 30 reaches its end-of-life. The elective replacement indicator can be report in any way that permits the clinician, patient, or both to use be aware of the elective replacement period such as annunciating 66 the elective replacement indicator with transceiver circuitry, an audible alarm, and the like. The elective replacement indicator can permit the implantable therapeutic substance infusion device 30 to be operated closer to an end-of-life period for the implanted therapeutic substance infusion device 30 thereby extending an effective life of the implantable therapeutic substance infusion device 30.

Figure 11:
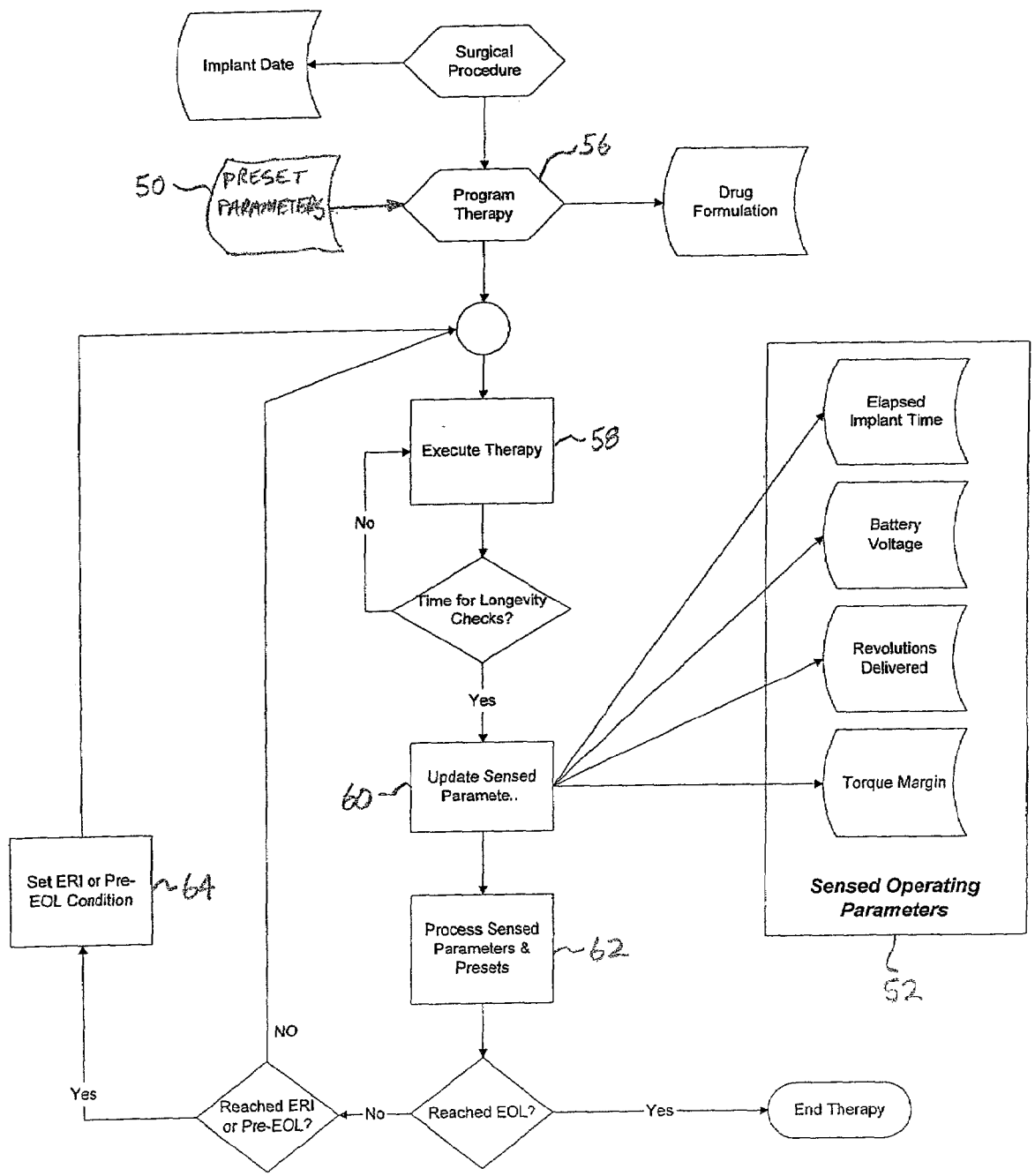
FIG. 11 shows a detailed block diagram for operating an implantable therapeutic substance infusion device embodiment with active longevity projection; and, FIG. 12 shows a block diagram of a longevity extension program for an implantable therapeutic substance infusion device embodiment with active longevity projection.

FIG. 11 shows a block diagram of a detailed implantable therapeutic substance infusion device with active longevity projection embodiment. The preset parameters 50 are typically stored 56 when the therapy is programmed. Operation 58 begins when the therapy is executed. Sensing 60 of the sensed parameter 52 occurs during updating of the sensed parameters. The elective replacement period is calculated 62 when the preset parameters 50 and sensed parameters 52 are processed. Reporting 64 of the elective replacement indicator can be done when the elective replacement indicator or pre-end-of-life condition is set.

Figure 12:
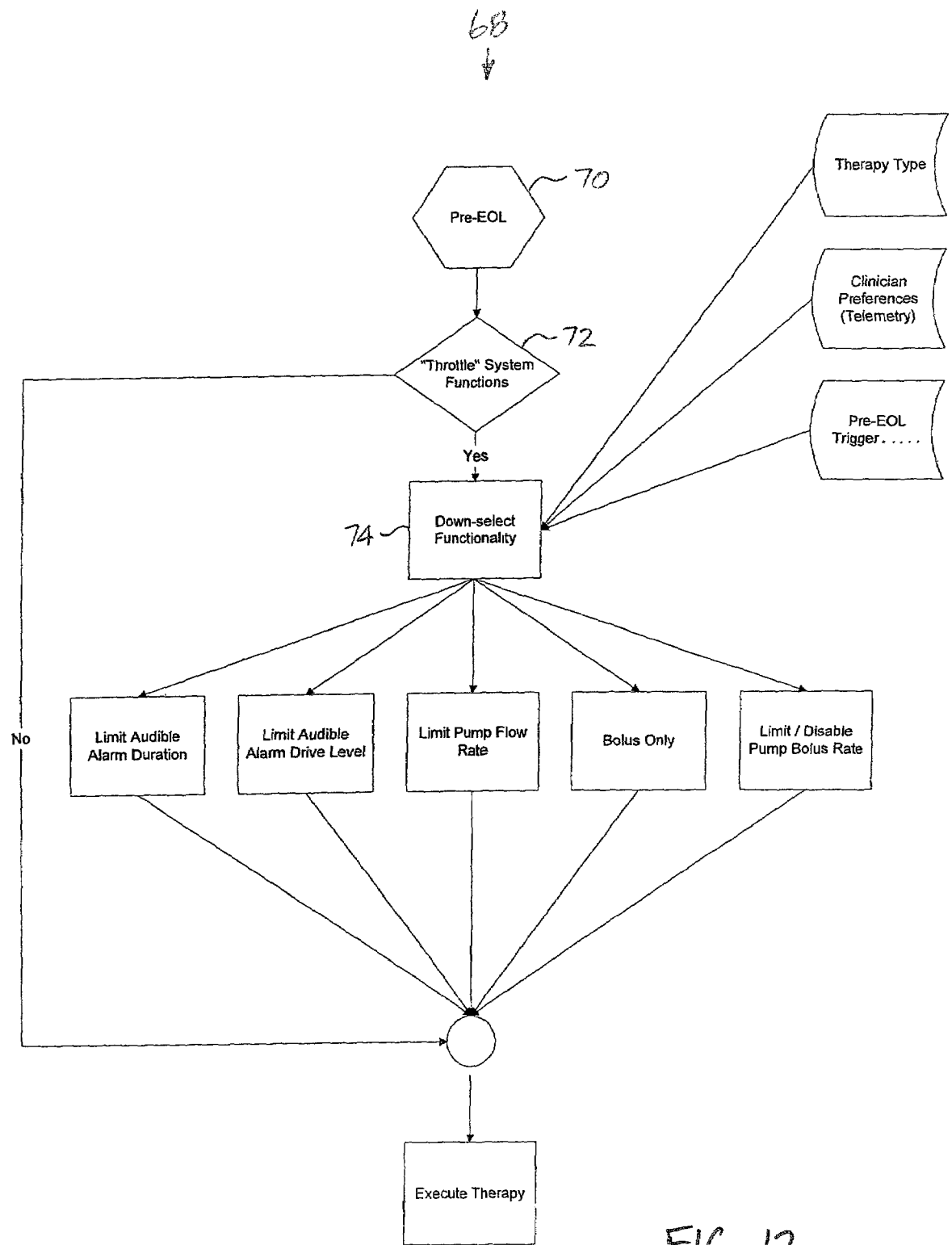

FIG. 12 shows a block diagram of a longevity extension program 68 residing in an implantable therapeutic substance infusion device 30 with active longevity projection embodiment. Operation of the longevity extension program begins when a pre-end-of-life (EOL) threshold has been met 70. The processor determines whether any of the infusion device functionality should be disabled or limited. Before the processor disables or limits functionality, the process determines whether any throttle system functions 72 established typically by the clinician should override the longevity extension program and cause the infusion device 30 to continue operation as programmed. Assuming the no throttle system function 72 is applicable to the pre-EOL circumstance, functionality is down selected 74 by disabling or limiting functionality according to preprogrammed preferences that can include therapy type preferences, clinician preferences, and pre-EOL event preferences. Functionality that may be disabled or limited includes audible alarm duration, audible alarm drive level, infusion pump flow rate, bolus operation, and bolus rate. After the functionality is disabled or limited, the therapy is executed.

Thus, implantable therapeutic substance infusion device 30 embodiments with active longevity projection more accurately predicts an elective replacement period for the infusion device 30 to increase the infusion device's 30 effective life, reduce the need for a clinician to perform static longevity forecasts for therapy changes, facilitate elective replacement scheduling for the convenience of the patient and clinician, and many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable therapeutic substance infusion device with active longevity projection, comprising:
   a housing;
   a power source carried in the housing;
   a therapeutic substance reservoir carried in the housing, the therapeutic substance reservoir configured for containing a therapeutic substance and being refilled with the therapeutic substance while implanted;
   a therapeutic substance pump carried in the housing, the therapeutic substance pump fluidly coupled to the therapeutic substance reservoir, and electrically coupled to the power source;
   electronics carried in the housing, the electronics coupled to the therapeutic substance pump and the power source, the electronics including,
      a processor,
      a memory coupled to the processor,
      an infusion program residing in the memory, the infusion program capable of being modified once the therapeutic substance infusion device is implanted;
      transceiver circuitry coupled to the processor for externally receiving and transmitting therapeutic substance infusion device information;
   at least one preset longevity parameter residing in the memory indicative of longevity of the implantable therapeutic substance infusion device;
   a monitor for sensing at least one sensed longevity parameter accessible by the processor and indicative of longevity of the implantable therapeutic substance infusion device wherein the sensed longevity parameter comprises therapeutic substance pump cycles,
   a longevity prediction program contained in the memory, the longevity prediction program correlating the preset parameter to the sensed parameter and calculating an elective replacement period for the implantable therapeutic substance infusion device; and
   a longevity extension program contained in the memory, the longevity extension program selectively implementing predetermined functional limitations to the implantable therapeutic substance infusion device based on the correlation of the sensed longevity parameter to the preset longevity parameter, to extend critical functionality of the implantable therapeutic substance infusion device beyond a calculated end-of-life period for the implantable therapeutic substance infusion device, wherein the predetermined functional limitations are selected from the group consisting of limit pump flow rate, and limit pump bolus rate.

2. A method for calculating an elective replacement period for an implantable therapeutic substance infusion device, comprising:
- storing at least one preset parameter accessible by a processor indicative of longevity for the implantable therapeutic substance infusion device;
- operating the therapeutic substance infusion device to infuse therapeutic substance into a patient;
- sensing at least one sensed parameter indicative of longevity for the implantable therapeutic substance infusion device wherein the sensed parameter comprises therapeutic substance pump cycles;
- calculating an elective replacement period for the implantable therapeutic substance infusion device by correlating the preset parameter with the sensed parameter; and,
- selectively implementing predetermined functional limitations based on the correlation of the preset parameter with the sensed parameter, to extend critical therapeutic substance infusion device functionality beyond a calculated end-of-life period for the implantable therapeutic substance infusion device, wherein the predetermined functional limitations are selected from the group consisting of limit pump flow rate, and limit pump bolus rate.

* * * * *